US008515530B2

(12) United States Patent
Warner et al.

(10) Patent No.: US 8,515,530 B2
(45) Date of Patent: Aug. 20, 2013

(54) SYSTEM AND METHOD OF NOISE DETECTION IN AN ELECTROCARDIOLOGY STUDY

(75) Inventors: Adrian F. Warner, Wauwatosa, WI (US); Daniel R. Schneidewend, Wauwatosa, WI (US); Claudio P. Mejia, Wauwatosa, WI (US); Timothy P. Stiemke, Wauwatosa, WI (US); Rodger F. Schmit, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 108 days.

(21) Appl. No.: 13/162,838

(22) Filed: Jun. 17, 2011

(65) Prior Publication Data

US 2012/0323130 A1 Dec. 20, 2012

(51) Int. Cl.
*A61B 5/04* (2006.01)

(52) U.S. Cl.
USPC ............................................. 600/509

(58) Field of Classification Search
USPC ............................................. 600/509
See application file for complete search history.

(56) References Cited

U.S. PATENT DOCUMENTS

| 4,420,815 A | 12/1983 | Francis |
| 2008/0045832 A1 | 2/2008 | McGrath |
| 2008/0315879 A1 | 12/2008 | Saha |

FOREIGN PATENT DOCUMENTS

WO 99/04688 A1 2/1999

OTHER PUBLICATIONS

Search Report and Written Opinion from PCT Application No. PCT/US2012/053268 dated Nov. 29, 2012.
Gholam-Hosseini et al., "ECG Noise Cancellation Using Digital Filters" Feb. 1998, 2nd International Conference on Bioelectromagnetism, pp. 151-152, http://www.mendeley.com/research/ecg-noise-cancellation-using-digital-filters-19/.

*Primary Examiner* — Carl H Layno
*Assistant Examiner* — Paula J Stice
(74) *Attorney, Agent, or Firm* — Patrick J. Kim; William T. Kryger (57) ABSTRACT

A system to use in combination with an ECG signal acquisition system is provided. The ECG signal acquisition system can be operable to connect to an arrangement of electrodes on a subject. The system can include a circuit board and a plurality of subcircuits mounted on the circuit board. The plurality of subcircuits can be arranged on the circuit board having an electrical impedance that correlate to an electrical impedance of the arrangement of electrodes on the skin surface of the subject. The system can further include an output connector connected in electrical communication to receive signals communicated from the plurality of subcircuits for communication to the ECG acquisition system.

9 Claims, 8 Drawing Sheets

SYSTEM AND METHOD OF NOISE DETECTION IN AN ELECTROCARDIOLOGY STUDY

FIELD OF USE

The subject matter generally relates to a system and method of noise detection, and more particularly to a system and method of detecting and identifying a direction of noise in a healthcare environment.

BACKGROUND

A setting, establishment and maintenance of a minimized noise levels in a work environment is a challenge and need of field engineers today. Examples of sources of noise interference can include ungrounded electrical extension chords, electrical sockets, equipment having a large electrical energy demand, etc. Such noise interference can often interfere with measurement and resolution of electrical signals taking place to conduct studies by processing equipment, or to test, debug, or maintain electrical signal processing equipment.

For example, one environment where noise is a concern can be in a healthcare setting where electrocardiology studies are taking place. Electrocardiogram (ECG) systems can measure small biopotential signals within a person's heart or at the surface of a person's skin. These biopotential signals can range as low as 100 uV, and can be resolvable to as little as 30 uV. For example, *Medical Instrumentation—Application and Method* by John G. Webster (1988) describes how electrodes can be located on a person (e.g., frontal plane or transverse plane) to track an ECG to be used as a diagnostic tool to examine functioning of the heart.

There is a need for an environment for processing equipment having minimized noise levels that can enhance electrical signal processing performance.

BRIEF SUMMARY

There is a need or desire a system and method to detect and locate sources of environmental noise that can interfere with measurement and resolution of electrical signals taking place to conduct studies by electrical signal processing equipment. The above-mentioned drawbacks and needs are addressed by the embodiments described herein in the following description.

According to one embodiment, a system to use in combination with an ECG signal acquisition system is provided. The ECG signal acquisition system can be operable to connect to an arrangement of electrodes on a skin surface of a subject. The system can include a circuit board and a plurality of subcircuits mounted on the circuit board. The plurality of subcircuits can be arranged on the circuit board having an electrical impedance that correlates to an electrical impedance of the arrangement of electrodes on the skin surface of the subject. The system can further include an output connector connected in electrical communication to receive signals communicated from the plurality of subcircuits for communication to the ECG acquisition system.

According to another embodiment of the subject matter described herein, a system including an ECG acquisition system in communication with an arrangement of electrodes in acquisition of an ECG signal of a subject is provided. The improvement includes an antenna system connected in communication with the ECG acquisition system, the antenna system including a series of subcircuits mounted on a circuit board. The series of subcircuits arranged on the circuit board can be analogous to the arrangement of electrodes on the subject. An output connector connects in electrical communication to receive a signal communicated from the plurality of subcircuits for communication to the ECG acquisition system for illustration of a bandwidth and an amplitude of the signal from the antenna system.

According to yet another embodiment, a system to detect a source of a noise interference signal with processing of an ECG acquisition system located in a defined space is provided. The system includes an antenna system that detects and communicates the noise interference signal to the ECG acquisition system; a location system connected to communicate an orientation and a location of the antenna system relative to the defined space; and a display configured to illustrate the measure of an amplitude of the noise interference signal in combination with an orientation and location of the antenna system relative to the defined space as the antenna system moves in the defined space.

Systems, methods, and computer program products of varying scope are described herein. In addition to the aspects and advantages described in this summary, further aspects and advantages will become apparent by reference to the drawings and with reference to the detailed description that follows.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
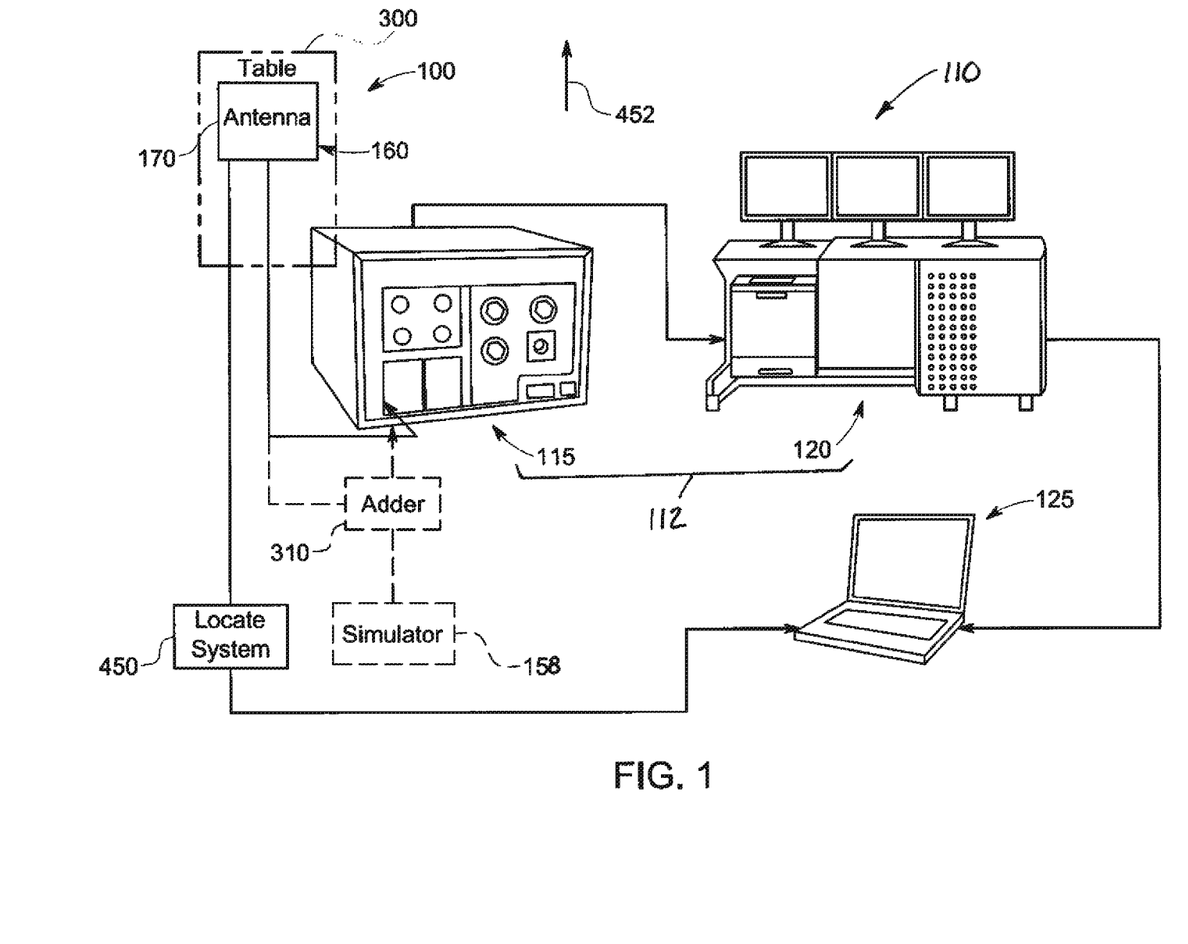
FIG. 1 shows a schematic diagram of an embodiment of a system operable to enhance detection, direction, and isolation of sources of noise interference in an electrical signal processing environment in accordance with the subject matter described herein.

FIG. 1 illustrates one embodiment of a system 100 operable to enhance detection, direction, and isolation of sources of noise interference in an electrical signal processing environment. An example of the electrical signal processing environment can be a biopotential study room where a subject 105 (e.g., person or animal) can undergo a study by a biopotential signal acquisition system 110. One example of the biopotential signal acquisition system 110 includes an electrocardiogram (ECG) signal acquisition system (surface or intracardiac) 112 as shown. Yet, other examples of types of biopotential signal monitoring systems can include but is not limited to systems for measurement of an electro encephalogram (EEG), electroneurogram (ENG), electromyogram (EMG), and electroretinogram (ERG) of a subject 105 (e.g., human or animal). Examples of sources of noise interference can include, but is certainly not limited to, ungrounded electrical extension cords, electrical sockets, high-energy consumption equipment, etc. The system 100 in combination with an ECG signal acquisition system 112 can be applied to various ECG signal acquisition applications such as stress test ECG, resting ECG, exercise ECG, patient monitoring, fibrulators, etc. involving sensitive electrical signal recording and processing.

For sake of example, the following description is of the ECG signal acquisition system 112 of the subject matter described herein can include wired or wireless communication of an amplifier 115, a recorder 120, and a series of electrodes 130 located at the subject 105. Yet, the recorder 120 is not required. The ECG signal acquisition system 112 can be connected in wired or wireless communication with an interface 125 of the system 100.

Examples of the biopotential signal acquisition systems 110 can be a Mac 3500, Mac 5500, Mac 400, CARDIOLAB™ EP Recorder, MAC 1600 ECG Monitor or the Solar 8000i Patient Monitor produced by GE™ Healthcare; the ELI 350 or X-Scribe produced by Mortara Instrument; the Burdick 8500 or Quniton Eclipse or Q9550 produced by Cardiac Science; the EP-Workmate Recording System produced by St. Jude; a GY Electrophysiology/EP recorder system produced by Henan Huanan Medical Science and Technology Co. Ltd.; the AXIOM SENSIS XP Hemo/EP recorder produced by SIEMENS™; the CARTO XP and CARTO 3 Mapping systems produced by BIOSENSE WEBSTER™; the Lab System Pro produced by BARD™ Electrophysiology; the Pagewriter TC30, TC50 or TC70, the IntelliVue MP40, MP50, MP60 and MP70, or the HeartStart MRx Monitor/Defibrillator produced by PHILIPS™; the 1500 Patient Monitor produced by Welch Allyn; or the Physio Control Lifepak 12 produced by MEDTRONIC™.

The electrodes 130 can be generally in contact with or coupled at a skin surface of the subject 105 and operable to acquire the ECG signals associated with cardiac activity of the subject 105. Each electrode 130 can be electrically connected to transmit the acquired ECG signals via a lead wire 135 to the amplifier 115. A known distribution of electrodes on the subject 105 can include right arm electrode 140, a left arm electrode 145, a right leg electrode 150, and a left leg electrode 155. Examples of the electrodes 130 can also be located internally either adjacent or at the heart of the subject 105.

The amplifier 115 can generally operate to receive input of the ECG signal, translate the ECG signal from analog to digital, increase the signal strength while maintaining high fidelity, and transmit the digitized ECG signal to the recorder 120 for further signal processing. The recorder 120 can generally perform signal processing for display and storage of the acquired ECG signal.

In another embodiment of the system 110, the amplifier 115 can be connected in communication to receive ECG signals transmitted from an ECG simulator 158 operable to recreate or simulate an ECG signal otherwise acquired from electrodes 130 on the subject 105. An example of the ECG Signal simulator 158 is produced by GE Healthcare, or the Multiparameter Patient ECG Simulator produced by the Fluke Corporation.

Figure 2:
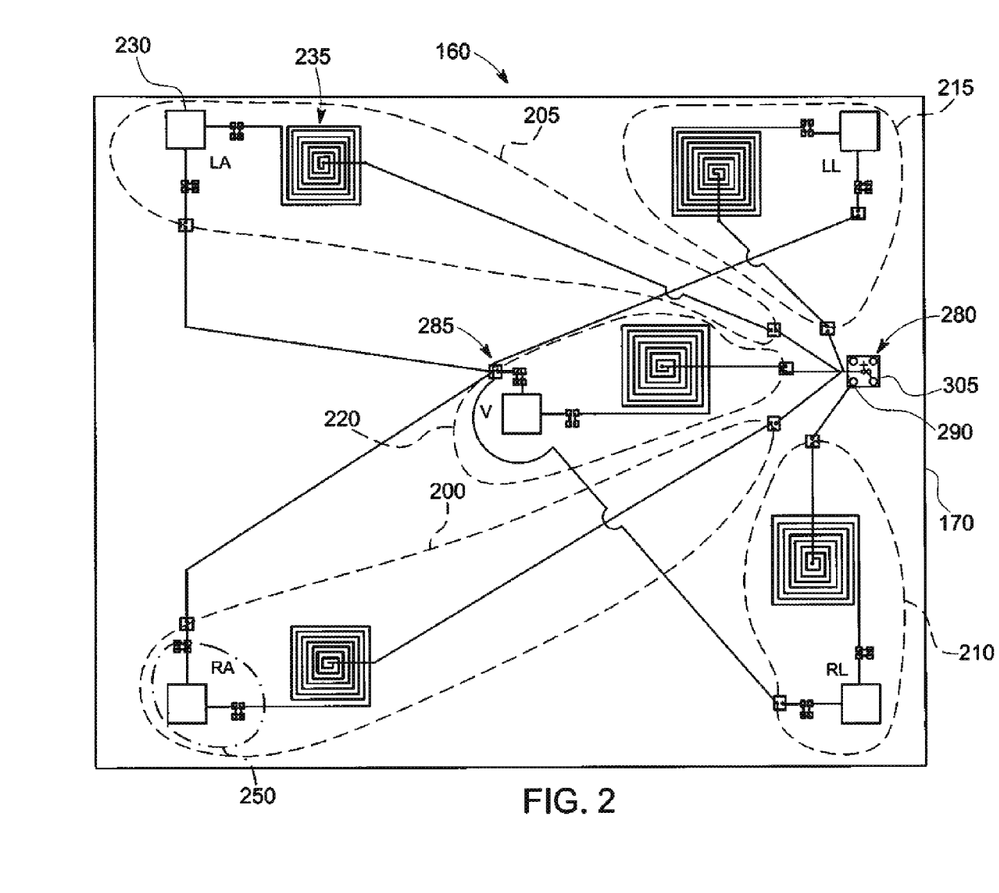
FIG. 2 shows a schematic diagram of one embodiment of an antenna system having an arrangement of electrical subcircuits on a circuit board to detect noise attenuation experienced by electrodes in acquisition of a biopotential signals emitted from a patient in accordance with the subject matter described herein.

Referring to FIG. 2, the system 100 can generally include an antenna system 160 electrically connected in communication with the amplifier 115 (See FIG. 1). An embodiment of the antenna system 160 can generally include an electrical circuit board 170 comprised of an electrical insulating substrate material configured to be mounted with or receive electrical subcircuits comprised of metallic etchings. The electrical circuit board 170 can be rectangular shaped and sized generally to be proportional to an average size of a person's torso 175. The dimensions and shape (e.g, polygon, circular, or combination thereof) of the electrical circuit board 170 can vary to accommodate for other physiological or environmental factors.

Still referring to FIG. 2, the antenna system 160 can further include a series of electrical subcircuits (described below) mounted on the circuit board 170 having objects or components that, solely or in combination, correlate to or operate as a proxy for the attachment of electrodes 130 and lead wires 135 leading from the subject 105 to the amplifier 115 in acquisition of an electrocardiogram signal from the subject 105.

An embodiment of the series of electrical subcircuits can generally correlate to a known topology or method (e.g., augmented leads in the frontal plane, precordial leads in the transverse plane) to place the electrodes 130 on the subject 105 so as to acquire the ECG signal. In one such example, the antenna system 160 can include first or right arm electrical subcircuit 200 that correlates to the electrode and lead wire 135 leading from the right arm (RA) of the subject 105, a second or left arm electrical subcircuit 205 that correlates to the electrode and lead wire leading from the left arm (LA) of the subject 105, a third or right leg electrical subcircuit 210 that correlates to the electrode and lead wire leading from the right leg (RL) of the subject 105, a fourth or left leg electrical subcircuit 215 that correlates to the electrode and lead wire leading from the left leg (LL) of the subject 105, and fifth or central terminal electrical subcircuit 220 that correlates to a central terminal (CT) as a point to measure an average of the acquired signals detected at the other three electrodes RA, LA and LL. The third electrical subcircuit 210 can be treated as a reference (e.g., electrical ground) to measure the electrical potential with respect to the signals acquired and detected at the first, second, and fourth electrical circuits 200, 205, 215 in an analogous manner as to how the RL electrode 150 can be used in tracking and performing a frontal plane ECG study.

Each of the electrical subcircuits 200, 205, 210, 215, 220 can include etched objects (described below) that in combination are configured to correlate to and have substantially (e.g., within twenty percent of a standardized electrical model of the patient electrode equivalent circuit) the same electrical impedance (including resistance, inductance and capacitive effect) as the use of electrodes 130 and lead wires 135 leading from the subject 105 to the amplifier in use in detection or acquisition of biopotential signals from the subject 105.

Referring to FIG. 2, an embodiment of one or more of the electrical subcircuits 200, 205, 210, 215, and 220 can include a first circuit component or object that exhibits an impedance that correlates to the impedance of the electrode 130 attached at the person's skin surface. The first circuit component or object 230 can be a metallic composition (e.g., copper etching) of similar size, shape, dimensions or surface area to correlate to the conductance of the electrode 130 that attaches at the subject 105. An embodiment of the first object 230 can be rectangular shaped, but the size, shape, dimension or surface area of the first object 230 can vary.

One or more of the electrical subcircuits 200, 205, 210, 215, and 220 can further include a second circuit component or object 235 having an electrical impedance that correlates to the impedance associated with the electrode lead wire 135 connecting the amplifier 115 to the electrode 130 attached at the subject 105. An embodiment of the second object 235 can be of length substantially similar to a length of the electrode wire. The second object 235 can be a metallic etch having a length arranged in a coil shape on the circuit board 170. The shape of the metallic etch of the coil can be polygonal (e.g., shown as square) or circular or serpentine shape or other shape and is not limiting.

Figure 3:
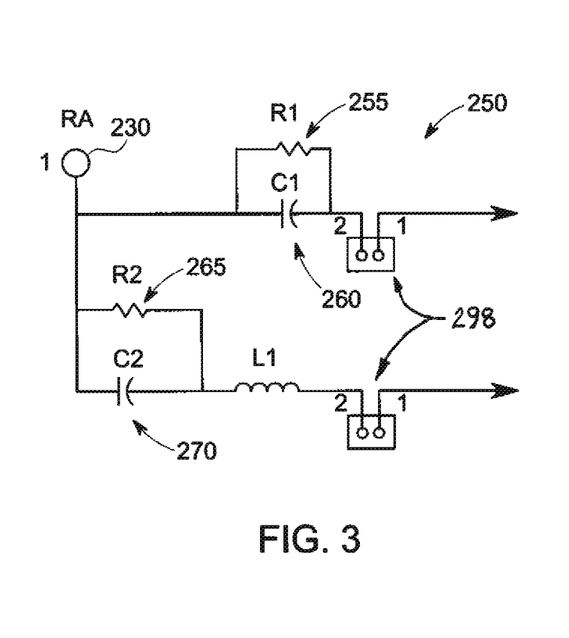
FIG. 3 illustrates a detailed schematic diagram of one embodiment of an electrical subcircuit to simulate an electrode located at a right arm in acquisition of biopotential signals from a patient in accordance with the subject matter described herein.

Referring to FIGS. 2 and 3, one or more of the electrical subcircuits 200, 205, 210, 215, and 220 can further include a subcircuit 250 comprising a first resistor 255 and capacitor 260 pair connected in electrical parallel connection and of electrical inductance and impedance value to correlate to the impedance (including resistance, capacitance, and inductance) associated with the impedance of the attachment of the electrode 130 to the skin or surface of the subject 105; and a second resistor 265 and capacitor 270 pair in electrical parallel connection to one another and of size such that the impedance can be substantially similar to an impedance of a bodily tissue that transmits electrical signals (e.g., associated with beating of the heart) through the subject 105. One embodiment of the impedance of the first resistor 255 and capacitor 260 pair can be of a threshold of an impedance value known in the industry associated with a poor attachment of the electrode 130 to the surface of the subject 105. Moreover, one embodiment of the thresholds of impedance of one or more of the subcircuits 200, 205, 210, 215, 220 can be of a value substantially equal to thresholds of published industry standards for impedance as defined for each correlative effect as defined herein.

Figure 4:
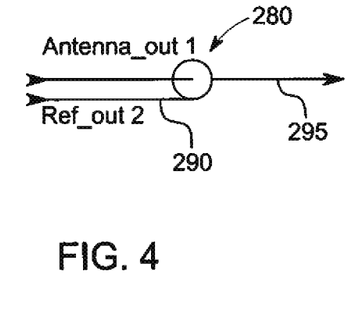
FIG. 4 illustrates a detailed schematic diagram of one embodiment of an antenna output of the antenna system of FIG. 3 in accordance with the subject matter described herein.

Referring to FIGS. 2, 3 and 4, an embodiment of the antenna system 160 can further include an electrical connection of an output from each of the first, second, third, fourth, and fifth electrical subcircuits 200, 205, 210, 215, and 220 to a combined antenna output connector 280 (See FIGS. 2 and 4) for communication to the amplifier 115. The antenna system 160 can further include an electrical connection of a common terminal 285 (See FIG. 2) from each of the first, second, third, fourth, and fifth electrical subcircuits 200, 205, 210, 215, and 220 in electrical connection to one another. The fourth electrical subcircuit 215 can include a reference terminal connection to an electrical reference or an electrical ground terminal 290 (See FIGS. 2 and 4) at the combined antenna output connector 280. An embodiment of the combined antenna output connector 280 can be a Bayonet Neill-Concelman (BNC) connector configured to receive a connection from a coaxial cable 295 (See FIG. 4) to communicate the acquired antenna signals to the amplifier 115. Yet, the type of connector 280 and communication link (e.g., wireless, wired) can vary. The coaxial cable 295 can include an electrical shield to isolate and inhibit contamination of the electrical signal from the antenna system 160.

Each of the first, second, third, fourth and fifth electrical subcircuits 200, 205, 210, 215, and 220 can include a pair of electrical connector terminals 298 that isolate connection or disconnection of the respective electrical subcircuits 200, 205, 210, 215, and 220 with the remainder on the circuit board 170. Thereby, each subcircuit 200, 205, 210, 215, 220 can be designed to provide discrete signal output of measured noise interference from each subcircuit 200, 205, 210, 215, 220 for sequential or parallel communication for illustration to the user at the recorder 120 or interface 125.

Another embodiment of the antenna system 160 can further include a second substrate layer or insulating layer separating the first substrate layer and electrical subcircuits mounted thereon from an electrical conducting layer connected to an electrical ground 305.

According to one embodiment as illustrated in FIG. 1, the antenna system 160 can be coupled to or constructed integrally with a table 300 in support of the subject 105 during acquisition of the ECG signal. Yet, another embodiment of the antenna system 160 can be independently constructed to be uncoupled and mobile to move in isolation of the patient table 300.

In another embodiment of the antenna system 160, output from each of the electrical subcircuits 200, 205, 210, 215, 220 of the antenna system 160 can be electrically connected to a switch mechanism (not shown) so as to automatically isolate the electrical potential across selective pairs of electrical subcircuits 200, 205, 210, 215, 220 in a manner similar to isolation of electrical potential across the electrodes 130 in tracking an electrocardiogram of the patient 105.

Figure 5:
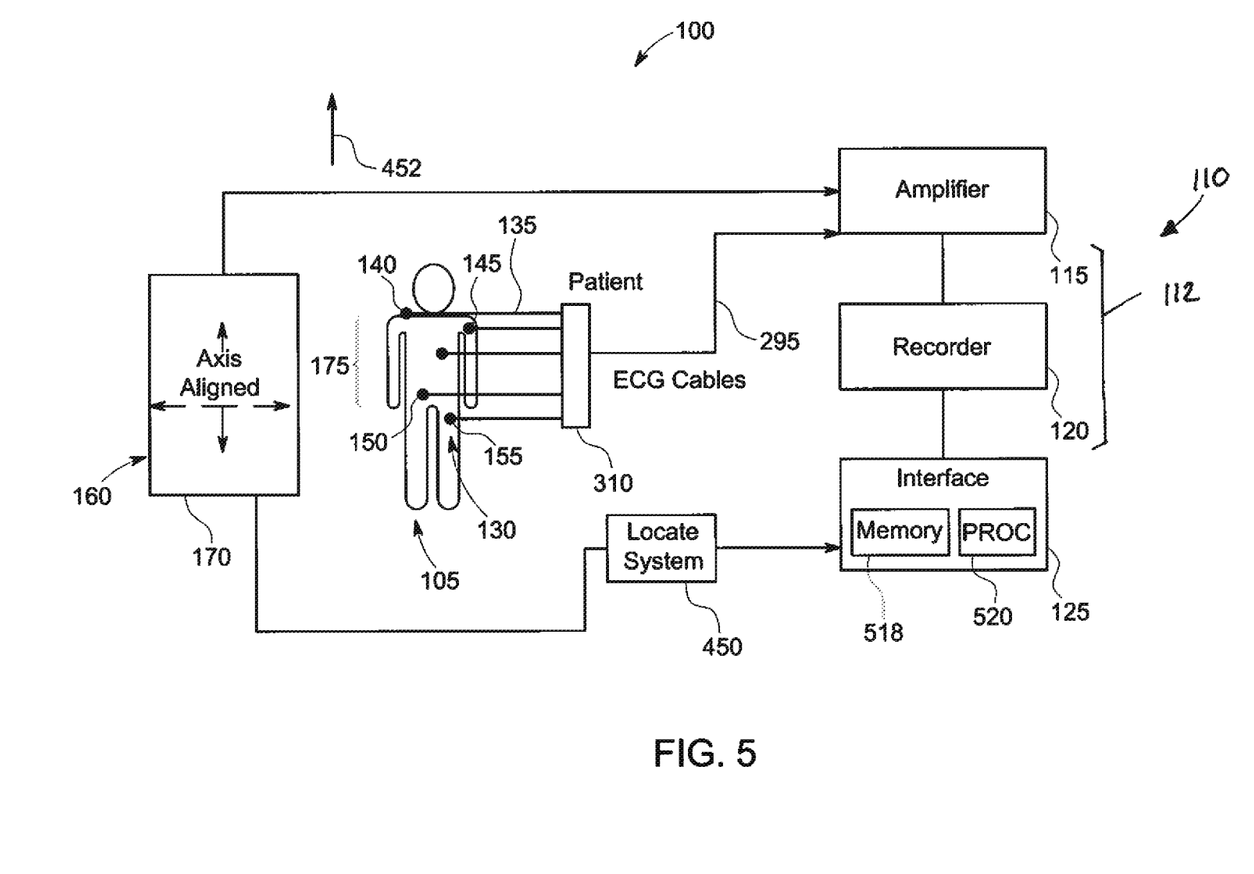
FIG. 5 shows a schematic diagram of an embodiment of the system of FIG. 1 operable to simulate acquisition and measurement of noise attenuation in a bipotential signal study of a patient in accordance with the subject matter described herein.

Referring to FIG. 5, the system 100 can further include the biopotential signal simulator 158 (e.g., ECG signal simulator) that, along with the electrical output line from the antenna system 160, can be in connected in communication with an adder or similar type of electrical signal mixing device 310 operable to selectively isolate or combine/mix one or more of the acquired signals from the simulator 158 and the antenna system 160 for communication to the amplifier 115 and recorder 120.

Referring to FIGS. 1 and 5, the interface 125 can be a laptop or general computer connected in communication with the ECG signal acquisition system 110, such as the recorder 120. The interface 125 can be operated by a field engineer or service technician working to diagnose and increase an operating efficiency of the ECG signal acquisition system 112, or identify sources of noise interference distorting the output from the ECG signal acquisition system 112.

Figure 6:
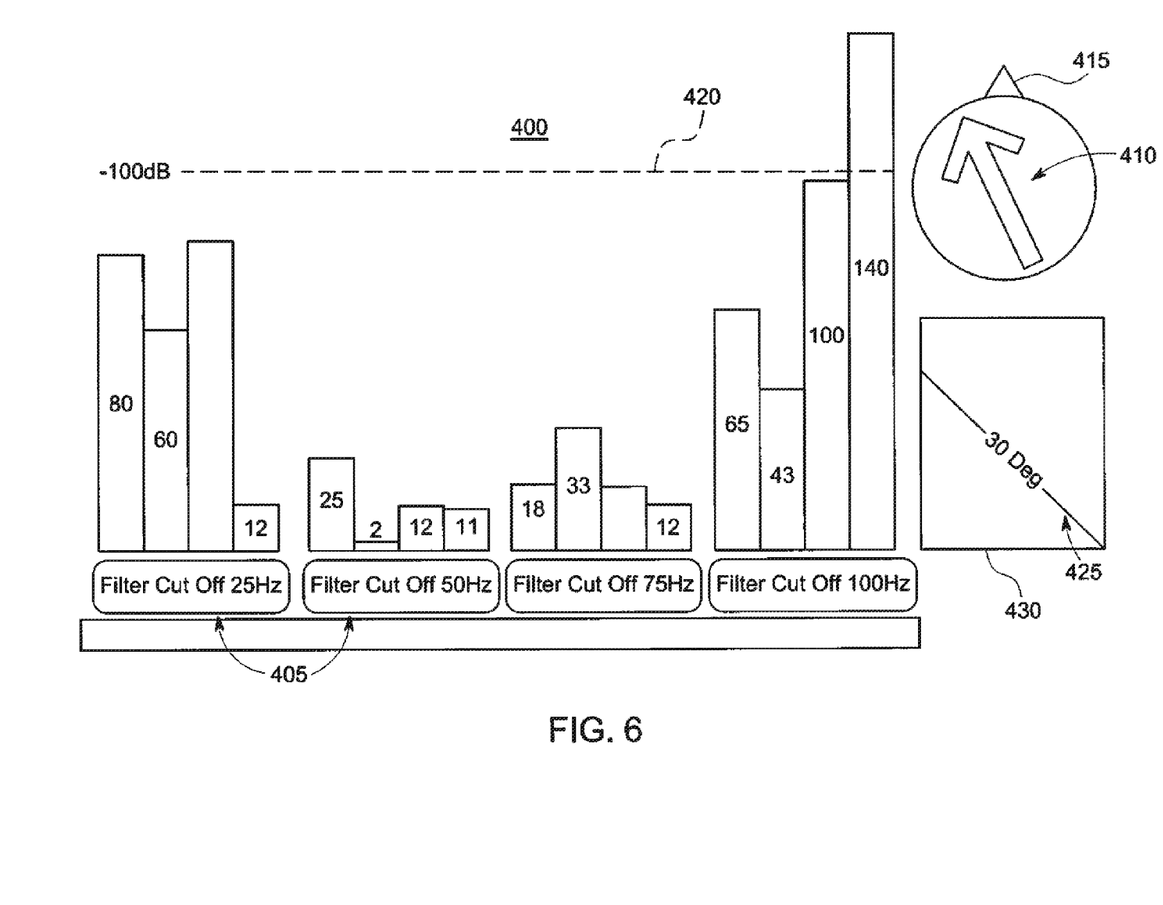
FIG. 6 shows an embodiment of a visual display output by the system of FIG. 1 in accordance with the subject matter described herein.

FIG. 6 illustrates an embodiment of a graphic display 400 generated by the system 100. The graphic display 400 can include graphic illustrations representative of a measure of different ranges or steps of filtration of cutoff frequencies 405 of the acquired electrical signals communicated from the antenna system 160 and/or simulator 158 for illustration at the ECG signal acquisition system 112 or at the interface 125 or both. The number of cutoff frequencies or ranges of filtration can vary and is not limiting on the subject matter described herein. The graphic display 400 can further include graphic illustrations representative of an orientation or direction of an alignment 410 of the circuit board 170 and mounted electrical subcircuits relative to a reference (e.g., alignment of the patient table 300 in a horizontal plane) 415 on the display 400. By rotating the circuit board 170 until detecting and measuring the largest intensity or amplitude 420 of electrical signals in the filtration or cutoff frequency range of noise, an operator can observe the graphic illustration of the orientation or direction of alignment 410 of the circuit board 170 that can point the observer to the direction of each source of noise in the space that can affect the results of ECG signal acquisition performed on the subject 105. The graphic display 400 can further include a visual graphic of a direction or orientation 425 of the circuit board 170 in the vertical direction relative to a reference (e.g., reference can be height level of the patient table 300) 430 on the display 400.

Referring to FIGS. 1 and 5, the system 100 can further include a location or tracking system 450 operable to track the location (e.g., rectangular x, y, z coordinates, latitude, longitude, height, etc.) and orientation (e.g., 180 or 360 degree angular alignment) of the antenna system 160 relative to a physical reference 452 of the space. Thereby, the tracking system 450 can support generation of the visual graphics 410 and 425 described above. The location system 450 can employ various types of known location tracking technologies (e.g., accelerometers, gyroscopes, cameras, RFID, ultrasound, electromagnetic, infrared, optical scanners, etc.) and is not limiting on the subject matter described herein. The location system 450 can communicate this location and orientation information of the antenna system 160 relative to the physical reference 452 in the defined space for illustration at the interface 125 to the user. Thereby, the system 100 can illustrate detection of the source of the noise interference signal with processing of the acquired ECG signals by the ECG monitoring system 112 relative to the reference 452 of the defined space. The antenna system 160 can be connected to communicate the noise interference signal to the ECG monitoring system 112 for communication at the interface 125. The location system 450 can be connected (e.g., wired or wireless) to communicate the orientation and location of the antenna system (e.g., the location and orientation of the circuit board 170) for combined illustration at the interface 125 of the largest amplitude 420 electrical signals in the cutoff frequency range of noise in combination with the orientation and location of the antenna system 160 with movement of the antenna system 160 in the defined space relative to the reference 452. Thereby, with movement of the antenna system 160 throughout the defined, the system 100 can illustrate via the interface 125 the detection and measure of the greatest noise interference signal within a defined bandwidth in combination with the location and orientation of the antenna system 160 (e.g., the circuit board 170) in general real-time with the detection and measurement of the noise interference signal.

Figure 7:
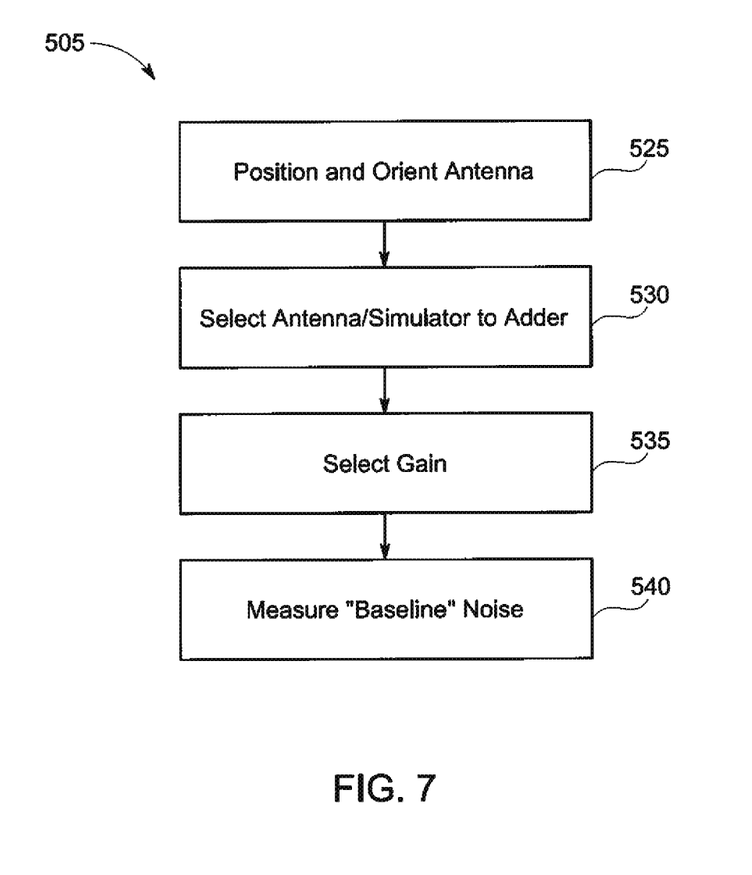
FIG. 7 shows a flow diagram of an embodiment of a method of acquiring a baseline noise measurement using the system of FIG. 1.
Figure 8:
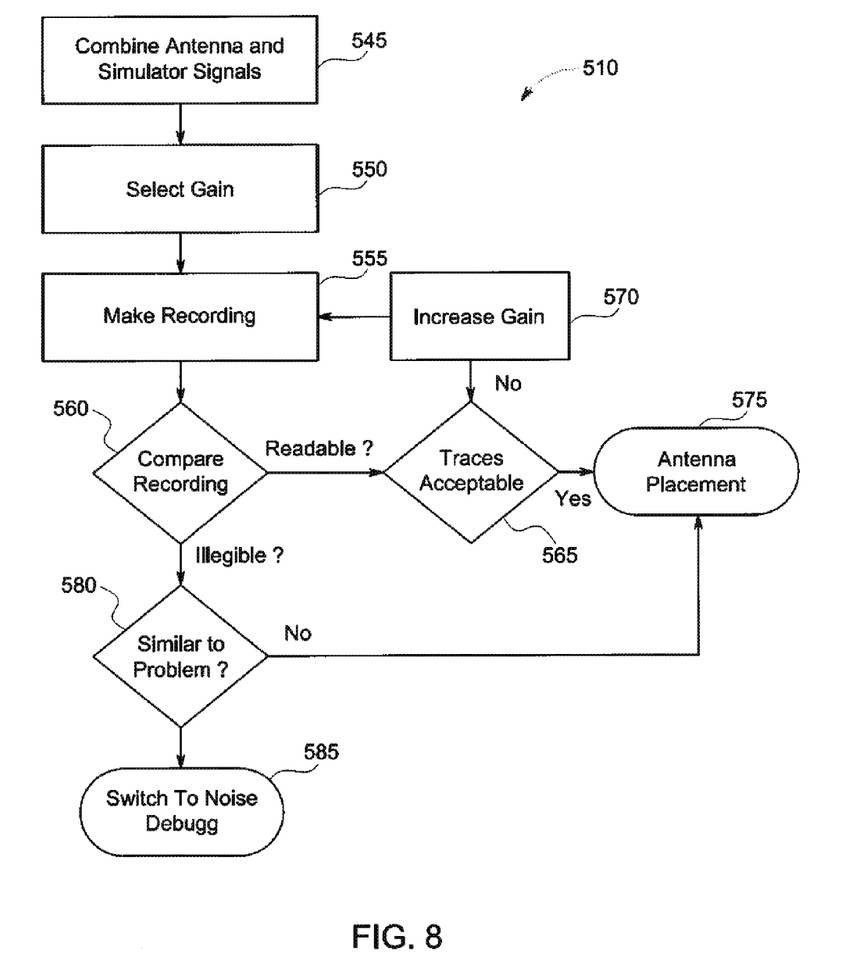
FIG. 8 shows a flow diagram of an embodiment of a method of performing noise simulation using the system of FIG. 1.
Figure 9:
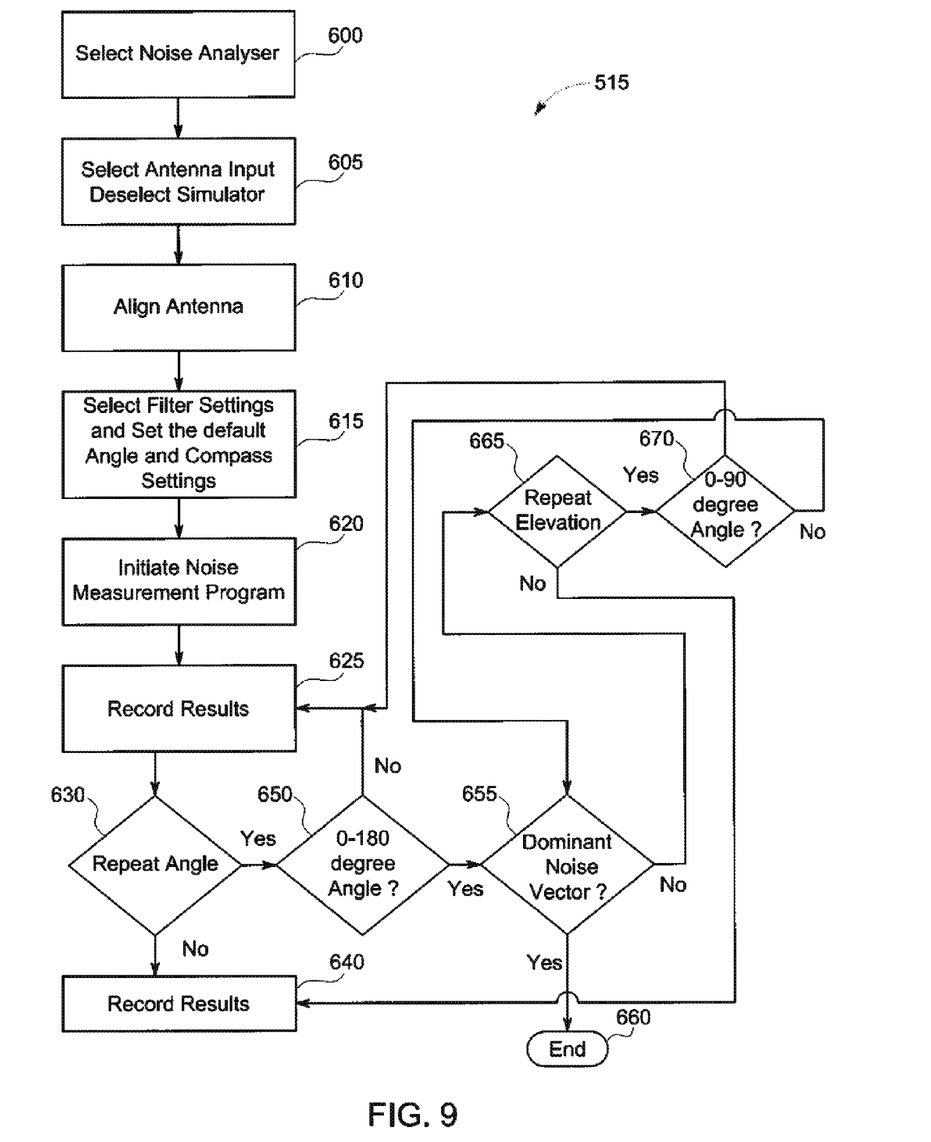
FIG. 9 shows a flow diagram of an embodiment of a method of performing noise angulation using the system of FIG. 1.

Having generally provided the above-description of a construction of the embodiments the system 100 of the subject matter described herein, the following is a general description of embodiment of methods 505, 510, 515 of operating the embodiment of the system 100 described above. It should also be understood that the sequence or succession of the acts or steps of the method as described in the foregoing description can vary. Also, it should be understood that the methods 505, 510, 515 may not require each act or step in the foregoing description, or may include additional acts or steps not disclosed herein. One or more of following steps and acts of the methods 505, 510, 515 can also be in the form of computer-readable program instructions stored in memory 518 for execution by a processor or other computer programmable device 520 either of the interface 125 or in communication therewith.

Assume that an ECG recorder 120 is coupled in communication with the amplifier 115 in an ECG study room or defined space. The method of operation includes connecting the simulator 158 and the antenna system in communication with the adder 310, and connecting the adder 310 in communication to the amplifier 115 and recorder 120. Also assume that the interface 125 can be connected in communication to receive the data communicated to the recorder 120.

FIG. 7 shows an embodiment of the method 505 of acquiring a baseline noise measurement using the system 100 described above. Step 525 includes positioning or orienting the antenna system 160 in correlation to a position or orientation of the subject to undergo the biopotential study. Step 530 includes connecting the antenna system 160 and the simulator in communication with the adder. Step 535 includes selecting at the adder to receive only the signal communicated from the simulator, and selecting desired amplifier gain setting to display simulator signal at the interface. Step 540 includes measuring and recording a baseline noise of within the system 100 for illustration at the display.

FIG. 8 shows an embodiment of the method 510 of performing a noise simulation. Step 545 includes switching the adder to communicate a combined signal from the signals received from the simulator and the antenna system 160. Step 550 includes selecting a gain at the recorder to display the combined signal from the adder. Step 555 includes receiving an instruction to make a recording of the combined signal for illustration at the interface. Step 560 includes comparing the recording to a known problem signal or report for encountered noise in electrical signal processing, and receiving an instruction if the combined signal is readable or illegible. Step 565 includes receiving an instruction whether the recording of the combined signal is acceptable. If the instruction indicates not readable, Step 570 includes increasing the setting for the gain at the recorder and returning to step 555. If the instruction indicates acceptable, step 575 includes placement and recording location of the circuit board of the antenna system 160. Step 580 includes comparing the recorded combined signal to the known problem signal or report. If receiving an instruction that the recorded combined signal is substantially similar to the problem signal or report, Step 585 includes switching or start of the method 515 described in FIG. 10. If receiving an instruction that the recorded combined signal is not substantially similar to the problem signal or report, then returning to step 575.

Referring now to FIG. 9 and the embodiment of the method 515 of performing noise debugging. Step 600 includes receiving an instruction of selection of noise analyzer functionality via the interface. Step 605 includes selecting to communicate the signal from the antenna system 160 only from the adder, and deselecting addition of the signal from the simulator. Step 610 includes locating the circuit board of the antenna system in general alignment with orientation and location of the subject 105 to undergo the biopotential study. Step 615 includes receiving instructions of selected filter ranges, and a set default angle and compass setting. Step 620 includes receiving an instruction to record the signal from the antenna system at the recorder. Step 625 includes receiving an instruction to record the signal analysis for illustration on the display. Step 630 includes receiving an instruction indicative to change an angle or orientation of the circuit board of the antenna system, and returning to step 620. If receiving an instruction of no further orientation changes to the circuit board, then step 640 includes recording the results of the signal analysis on the display and returning to step 610. If receiving an instruction to change the orientation of the circuit board of the antenna system and performing signal analysis on the signal from the circuit board, step 650 includes measuring a change of orientation of the circuit board relative the reference for illustration on the display. Step 655 includes detecting if the current orientation of the circuit board relative to the reference creates largest or dominant noise vector compared to analysis of signals for other orientations of the circuit board. If the dominant noise vector, step 660 is the end of the method. If not the dominant noise vector, step 665 includes recording a change in elevation of the circuit board relative to the reference and proceeding to step 640 to record the results of the signal analysis in the display. Step 670 includes recording a change in orientation of the circuit board in a vertical plane relative to a reference, and proceeding to step 640 to record the results of the signal analysis in the display.

A technical effect of the above-described embodiments of the subject matter described above can include providing the system 100 and method to mimic an effect of, detect, and locate sources of noise related interference in an environment to perform electrical signal tracking and processing such as an electrophysiological study room where an ECG can be measured of the subject 105. The ability to detect and isolate a location of the source of noise interference in an ECG study environment can enhance procedural results, reduce the time to complete an ECG case study. The system 100 and method can also enhance the servicing, maintenance, and debugging poor performance of the ECG y recording systems 120.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system to use in combination with an ECG signal acquisition system operable to connect to an arrangement of electrodes on a subject, the system comprising:
    a circuit board;
    a plurality of subcircuits mounted on the circuit board, the plurality of subcircuits arranged on the circuit board having an electrical impedance that correlates to an electrical impedance of the arrangement of electrodes on the subject; and
    an output connector connected in electrical communication to receive signals communicated from the plurality of subcircuits for communication to the ECG signal acquisition system.

2. The system of claim 1, wherein each of the plurality of subcircuits has the electrical impedance within a predefined threshold of at least one electrode in the arrangement of electrodes on the subject.

3. The system of claim 1, wherein each of the plurality of subcircuits includes an electrical component having an electrical impedance within a predefined threshold of the electrical impedance of an attachment of at least one electrode in the arrangement of electrodes on the subject.

4. The system of claim 1, wherein at least one of the electrical subcircuits includes a pair of disconnects that when open isolates the respective electrical subcircuit from the output connector.

5. The system of claim 1, wherein each of the electrical subcircuits includes a metallic etch of a length substantially equal to a length of a lead wire connecting the ECG acquisition system to the arrangement of electrodes.

6. The system of claim 1, further comprising an interface connected in communication with the ECG acquisition system, the interface including a display of at least one range of electrical signals detected within one of a predefined wavelength or a frequency that are communicated from the output connector.

7. The system of claim 6, the display further comprising a graphic illustration of a unique alignment of the circuit board relative to a reference of a defined space.

8. The system of claim 7, wherein the reference is one of a horizontal plane and a vertical plan.

9. The system of claim 1, further comprising a display configured to illustrate the measure of amplitude of the signal in combination with an orientation and location of the circuit board relative to a defined space as the circuit board moves in a defined space.

* * * * *